United States Patent [19]

Nohira et al.

[11] Patent Number: 4,917,817
[45] Date of Patent: Apr. 17, 1990

[54] OPTICAL ACTIVE COMPOUND, PROCESS FOR PRODUCING SAME AND LIQUID CRYSTAL COMPOSITION CONTAINING SAME

[75] Inventors: Hiroyuki Nohira, Urawa; Masanao Kamei, Annaka; Hideki Kanazawa, Yotsukaichi; Tetsuya Abe, Kitaibaraki; Yoko Yamada, Atsugi; Yuko Etoh, Tokorozawa, all of Japan

[73] Assignee: Canon Kabushiki Kaisha, Tokyo, Japan

[21] Appl. No.: 222,426

[22] Filed: Jul. 21, 1988

[30] Foreign Application Priority Data

Jul. 24, 1987 [JP] Japan ................................. 62-183485
Jul. 24, 1987 [JP] Japan ................................. 62-183486
Feb. 22, 1988 [JP] Japan ................................. 63-037624

[51] Int. Cl.$^4$ ................. C09K 19/52; G02F 1/13; C07B 53/21
[52] U.S. Cl. .............. 252/299.01; 252/299.5; 252/299.66; 350/350 S; 560/55; 560/59; 560/75; 560/102; 560/111; 560/141; 560/144; 560/145; 562/469; 562/471; 562/472; 562/474; 562/605; 558/260; 568/642; 568/655; 568/842
[58] Field of Search ........... 252/299.01, 299.5, 299.66; 350/350 S; 560/55, 59, 75, 102, 111, 141, 144, 145; 562/469, 471, 472, 474, 605; 558/260; 568/642, 655, 842

[56] References Cited

U.S. PATENT DOCUMENTS 4,613,209 9/1986 Goodby et al. ............... 252/299.01

FOREIGN PATENT DOCUMENTS 264080 4/1988 European Pat. Off. .
248335 2/1987 Fed. Rep. of Germany ........... 252/299.01
3534778 4/1987 Fed. Rep. of Germany ........... 252/299.01
61-254533 11/1986 Japan ............... 252/299.01
61-254537 11/1986 Japan ............... 252/299.01
61-254544 11/1986 Japan ............... 252/299.01
62-192329 8/1987 Japan ............... 252/299.01
1308237 2/1973 United Kingdom ........... 252/299.68

OTHER PUBLICATIONS

Goodby, J. W., et al, Liquid Crystals and Ordered Fluids, vol. 4, Griffin, A., et al., Ed., Plenum Press, N.Y., pp. 1–32 (1985).
Weinges, K., et al., Liebigs Ann. Chem., pp. 90–102 (1985).
Kitazume, T., et al., Chem. Lett., pp. 237–238 (1983).
Taguchi, T., et al., Tetraheoron Lett., vol. 27, No. 42, pp. 5117–5120 (1986).
Walborsky, H. M., et al., J. Am. Chem. Soc., vol. 77, pp. 3637–3640 (1955).
Muller, N. J. Pharm. Sciences, vol. 75, No. 10, pp. 987–991 (1986).

Primary Examiner—Teddy S. Gron
Attorney, Agent, or Firm—Fitzpatrick, Cella, Harper & Scinto

[57] ABSTRACT

An optically active functional compound represented by the following formula (1) is disclosed:

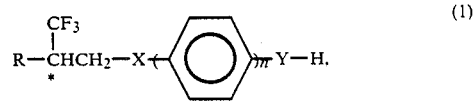

(1)

wherein R denotes an alkyl group having 1–14 carbon atoms; -X- denotes

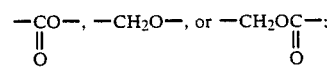

denotes a single bond,

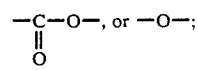

$n = 0$, 1 or 2; and C* denotes an asymmetric carbon atom. The compound of the formula (1) may be produced through an optically active compound of the following formula (2) or (3):

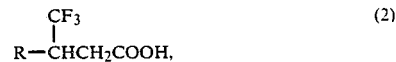

(2)

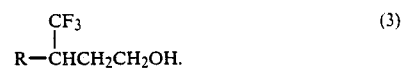

(3)

The compounds of the above formulas (1)–(3) are all characterized by a trifluoromethyl group providing a large spontaneous polarization attached to an asymmetric carbon atom.

4 Claims, No Drawings

OPTICAL ACTIVE COMPOUND, PROCESS FOR PRODUCING SAME AND LIQUID CRYSTAL COMPOSITION CONTAINING SAME

FIELD OF THE INVENTION AND RELATED ART

The present invention relates to a novel optically active compound, a process for producing the same and a liquid crystal composition containing the optically active compound.

There have been known various types of optical devices characterized by having optical activities as will be exemplified as follows:

(1) Those utilizing a cholesteric-nematic phase transition in a liquid crystal state (J.J. Wysoki, A. Adams and W. Haas: Phys. Rev. Lett., 20, 10204 (1968));

(2) Those utilizing a guest-host effect of the White-Taylor type in a liquid crystal state (D.L. White and G.N. Taylor: J. Appl. Phys., 45, 4718 (1974));

(3) Those utilizing a ferroelectric liquid crystal effect of a chiral smectic C phase, H phase, F phase, I phase or G phase (N.A. Clark and S.T. Lagerwall: Appl. Phys. Lett., 36, 899 (1980));

(4) Others including notch filters or band path filters utilizing selective scattering characteristics of a material having a cholesteric phase in the liquid crystal state when fixed in a matrix (F.J. Kahn: Appl. Phys. Lett. 18, 231 (1971)): and circular polarization beam splitters utilizing circular polarization characteristics (S.D. Jacobs, SPIE, 37, 98 (1981)).

These optical devices are important as display devices and modulation devices, while the explanation of the individual systems is left to the respective references and omitted.

Functional materials constituting these optical devices contain an optically active compound or substance as a major component thereof or as a component which is used in a relatively small proportion but constitutes a functionally important part. For example, it has been disclosed to add another optically active compound or mesomorphic compound into an optical device material as described above, particularly a liquid crystal material, to control the kind and the temperature range of a liquid crystal phase developed in its liquid crystal state (H. Arnold, Z. Phys. Chem., 226,146 (1964)). It is further expected to add a compound having a large dipole moment into a liquid crystal material driven in response to an electric field to obtain a liquid crystal material having a better electric field-responsive characteristic.

However, many of the known optically active compounds are not easy to change the length of an introduced group and therefore are not suitable for controlling the liquid crystal state.

Many of such optically active functional compounds are synthesized through an intermediate which per se is optically active.

Heretofore, as optically active intermediates for synthesizing functional materials necessary for such optical devices characterized by optical activity, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives.

However, these intermediates involve respective problems as follows. Thus, optically active chain hydrocarbon derivatives are difficult to modify their structures and very expensive except for a particular class thereof. Amino acid derivatives are relatively cheap and easy to modify their structures, whereas N-hydrogens therein are chemically active and liable to cause hydrogen bonding or other chemical reactions so that the performances of the resultant functional material can be restricted thereby. Camphor derivatives and cholesterol derivatives are difficult to modify the structures and the steric hindrance is liable to provide ill effects to the performances of the resultant functional materials.

Further, for a class of optical devices utilizing an electric field-responsive optical effect in a liquid crystal state, it has been practiced to introduce a polar group, whereas most of the above mentioned conventional optically active intermediates has a small polarity or have a structure where the polar group cannot be effectively utilized.

It has been especially known for a ferroelectric liquid crystal that the response speed is proportional to its spontaneous polarization, so that it is desired to increase the spontaneous polarization for achieving a high speed driving. From such a viewpoint, P. Keller et al have shown that it is possible to realize a higher response speed through increase in spontaneous polarization by introducing a chlorine atom so as to be bonded to an asymmetric carbon atom (C.R. Acad. Sc. Paris, 282 C, 639 (1976)).. However, the chlorine atom bonded to the asymmetric carbon atom is chemically unstable and has a large atomic radius so that the stability of the liquid crystal phase is lowered. Accordingly, an improvement is still desired.

SUMMARY OF THE INVENTION

A principal object of the present invention is, in view of the above problems, to provide a useful optically active compound which not only is useful as an appropriate optically active intermediate but also provides a high stability and a large spontaneous polarization when synthesized into a mesomorphic compound; a process for producing the same; and a liquid crystal composition containing the same.

A specific object of the present invention is to provide a compound showing an excellent electric filed response by attaching a group having a large dipole moment to an asymmetric carbon atom.

Another object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold: Z. Phys. Chem., 226, 146 (1964), and a liquid crystal composition containing at least one of such mesomorphic compounds.

A further object of the present invention is to provide a compound capable of easily controlling the hydrophobic group and being stably formed into a film when applied to the LB (Langmuir-Blodget) film process for preparing an accumulation of single molecular films.

First of all, the present invention provides an optically active compound represented by the following formula (1):

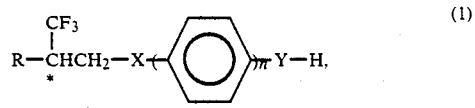
(1)

wherein R denotes an alkyl group having 1-14 carbon atoms; —X— denotes

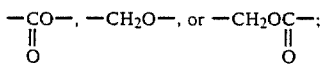

Y denotes a single bond,

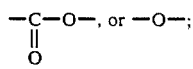

n=0, 1 or 2; and C* denotes an asymmetric carbon atom.

The compound represented by the formula (1) not only has functions of controlling a liquid crystal state and improving electric field responsive characteristics as described above, but also is expected to be used for synthesizing various derivatives without losing its optical activity by combining it with other functional intermediates.

The present invention also provides an optically active 3-trifluoromethylalkanoic acid of the following formula (2):

In the above formula and the formulas appearing hereinafter, R denotes an alkyl group having 1-14 carbon atoms and C with * denotes an asymmetric carbon atom.

The present invention further provides an optically active 3-trifluoromethyl-1-alkanol of the following formula (3):

The compounds represented by the formulas (2) and (3) have an asymmetric carbon atom and a carbonyl group or hydroxyl group connected through a methylene group so that it can be readily converted without losing its optical activity into various derivatives through an ester bond, an ether bond, a urethane bond, a carbonate bond, etc., and therefore are expected to be widely utilized.

These optically active compounds represented by the formulas (2) and (3), however, have not been known heretofore. As a result of our intensive study, we have succeeded in synthesis of these compounds and arrived at the present invention.

Thus, the present invention further provides processes for providing the compounds of the above formulas (2) and (3), wherein trifluoroacetic acid as a starting compound is used to synthesize a racemic mixture of the compound of the formula (2), the racemic mixture is subjected to optical resolution to obtain the optically active compound of the above formula (2), and the compound is further reduced to obtain the optically active compound of the above formula (3).

The optically active compounds represented by the formulas (1), (2) and (3) not only are useful optically active intermediates but also are useful liquid crystal components by themselves. For example, when they are added in a very small amount in a nematic liquid crystal composition for a TN (twisted nematic)-type display device, the occurrence of a fringe pattern (reverse domain) may be effectively prevented to uniformize the display.

Thus, the present invention also provides a liquid crystal composition containing an optically active compound represented by the formula (1), (2) or (3).

The above mentioned and other objects and features of the invention will be better understood upon consideration of the following detailed description concluding with specific examples of production.

DETAILED DESCRIPTION OF THE INVENTION

In order to produce optically active compounds of the above formulas (2) and (3) according to the present invention, trifluoroacetic acid may be used as a starting material and reacted with an alkylmagnesium bromide or chloride at a low temperature (15° C. or below) to obtain a compound of the following formula (4):

Next, the compound of the formula (4) is reacted with ethyl acetate-triphenylphosphonium bromide to obtain a compound of the following formula (5):

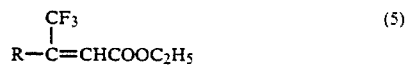

Then, the above compound of the formula (5) is successively subjected to hydrogenation and hydrolysis to obtain a racemic mixture of a 3-trifluoromethyl alkanoic acid of the above formula (2).

The optical resolution of the alkanoic acid or carboxylic acid may be easily effected by forming a diastereomer salt with an optically active base. Thus, the carboxylic acid may be subjected to optical resolution with a basic optical resolver agent such as (+) or (−)-1-phenylethylamine, whereby an optically active compound of the above formula (2) can be obtained.

Further, the optically active compound of the formula (2) may be further reduced to obtain an optically active compound of the above formula (3).

The above-mentioned series of reactions may be summarized by the following reaction scheme:

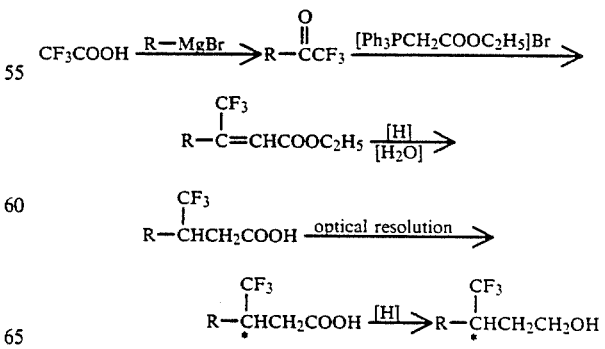

The optically active compounds of the formulas (2) and (3) according to the present invention can have a wide variety of R by changing the number of carbon atoms in the alkane moiety in the starting alkylmagnesium bromide or chloride but may preferably have an alkyl R of 1-14 carbon atoms, particularly 1-10 carbon atoms.

Further, the compound of the formula (1) may be synthesized from an optically active intermediate of the following formula (6):

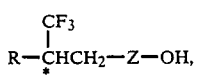 (6)

wherein R denotes an alkyl group having 1-14 carbon atoms, and Z denotes

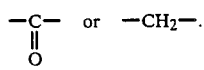

The reaction may be represented by the following reaction scheme:

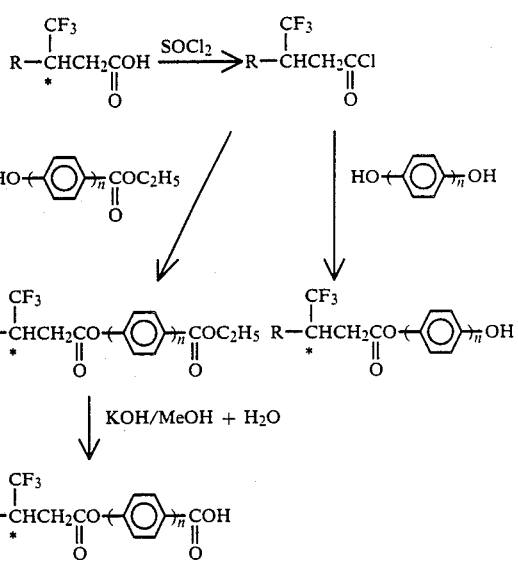

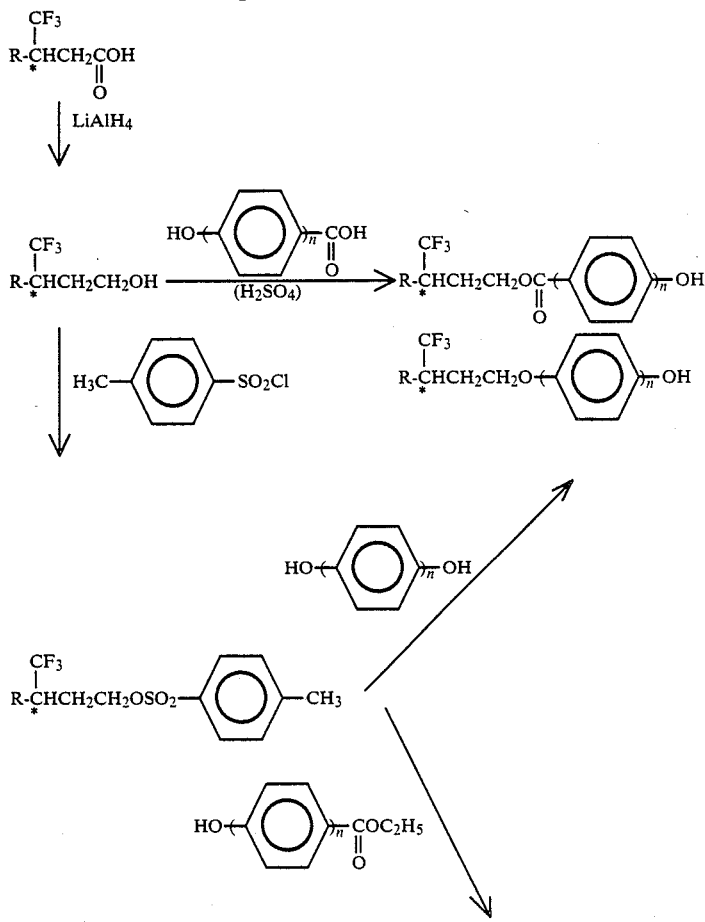

-continued

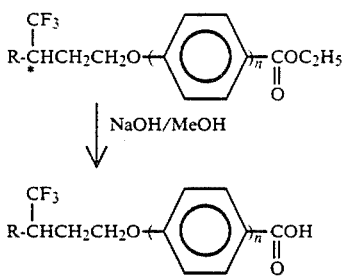

R and n are the same as defined above.

The optically active compounds of the formulas (1), (2) and (3) may have an alkyl group R having 1-14 carbon atoms, preferably 1-10 carbon atoms, further preferably 1-8 carbon atoms, most preferably 4-6 carbon atoms.

As has been briefly mentioned hereinbefore, the optically active compounds represented by the formulas (1), (2) and (3) may be used instead of a conventionally used optically active compound such as a hydrocarbon chain derivative, an amino acid derivative, a camphor derivative, or a cholesterol derivative, and may be connected with another intermediate through ester bond, ether bond, urethane bond, carbonate bond, etc., by using a releasable reactive group such as carboxyl group or hydroxyl group. For this reason, the optically active compounds are not only useful as an intermediate for producing functional materials constituting optical devices, but also useful as an intermediate for synthesizing various natural optically active compound.

Further, the optically active compounds represented by the formulas (1), (2) and (3) are effectively used for preventing generation of reverse domain in a TN-type cell by adding them into a nematic liquid crystal. In this case, the optically active compound of the formula (1), (2) or (3) may preferably be used in a proportion of 0.01-50 wt. % of the resultant liquid crystal composition.

Further, the optically active compound may be used to form a chiral nematic liquid crystal composition for use in a phase-transition type liquid crystal device or guest-host type liquid crystal device of the White-Taylor type by adding it into a nematic or chiral nematic liquid crystal. In this case, the optically active compound of the formula (1), (2) or (3) may preferably be used in a proportion of 0.01-80 wt. % of the resultant liquid crystal composition.

Further, the optically active compound of the formula (1), (2) or (3) may be added to a liquid crystal material showing a ferroelectric chiral smectic liquid crystal state by itself in a proportion of 0.01-80 wt. % of the liquid crystal composition to form a liquid crystal composition with improved characteristics such as durability.

Furthermore, the optically active compound of the formula (1), (2) or (3) may be added to a smectic liquid crystal including those shown below at (1)-(5) with structural formulas and phase transition temperatures (° C.), to provide a liquid crystal composition showing a ferroelectric chiral smectic phase. In this case, the optically active compound of the formula (1), (2) or (3) may be used in a proportion of 0.01-80 wt. % of the resultant liquid crystal composition. When the optically active compound of the formula (1), (2) or (3) is added to provide a chiral smectic liquid crystal composition in the manner as described above, the liquid crystal composition can have a large spontaneous polarization, a shorter response time, and a lower threshold voltage.

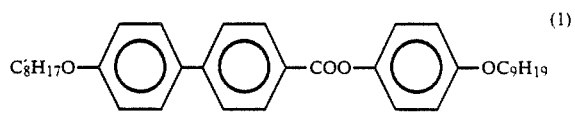

(4-nonyloxyphenyl)-4'-octyloxybiphenyl-4-carboxylate

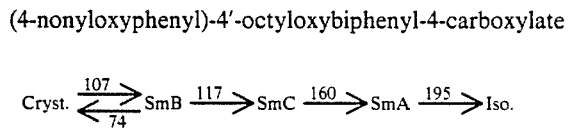

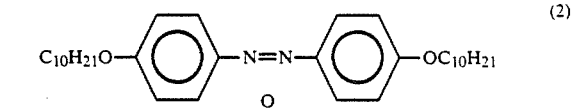

4,4'-decyloxyazoxybenzene

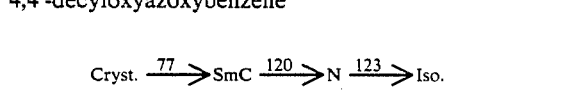

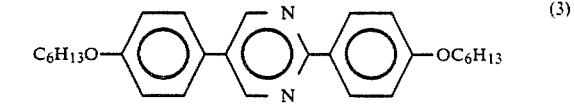

2-(4'-hexyloxyphenyl)-5-(4-hexyloxyphenyl)-pyrimidine

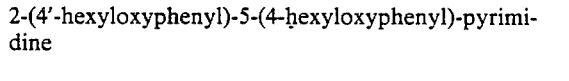

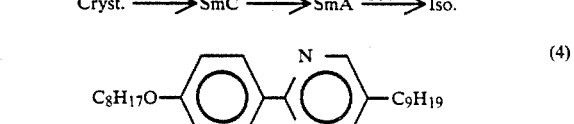

2-(4'-octyloxyphenyl)-5-nonylpyrimidine

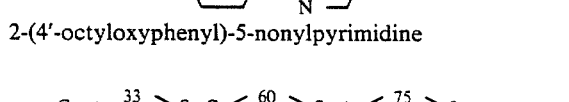

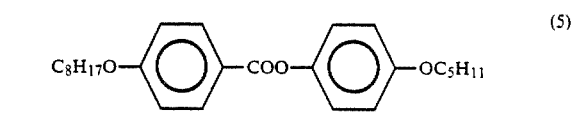

4'-pentyloxyphenyl-4-octyloxybenzoate

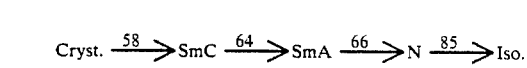

Herein, the symbols respectively denote the following phases:
Cryst.: crystal phase
SmA smectic A phase
SmB smectic B phase
SmC smectic C phase
N nematic phase
Iso. isotropic phase As described above, according to the present invention, there are provided optically active compounds represented by the formulas (1), (2) and (3) which have a trifluoromethyl group providing a large dipole moment directly attached to an asymmetric carbon atom.

Further, by the addition of at least one species of the optically active compounds represented by the formulas (1), (2) and (3), the generation of a reverse domain in a TN-type liquid crystal composition may effectively be prevented, or the electric field responsive characteristic of a chiral nematic liquid crystal or a chiral smectic liquid crystal may be improved, and the liquid crystal state of these liquid crystals may be controlled.

Hereinafter, the present invention will be more specifically explained with reference to specific examples of production.

EXAMPLE 1

Optically active 3-trifluoromethylheptanoic acid was produced through the following reaction steps (1)–(5):

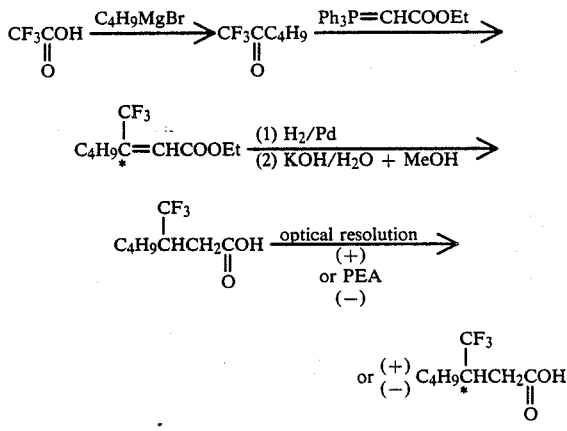

(1) Production of 1,1,1-trifluoro-2-hexanone.

In a nitrogen atmosphere, 9.12 g (380 mM) of magnesium into 120 ml of ether, and 49.32 g (360 mM) of butyl bromide dissolved in 30 ml of ether was added thereto, followed by 1.5 hours of heat refluxing. After cooling by standing and with ice, 13.68 g (120 mM) of trifluoroacetic acid dissolved in 30 ml of ether was added. After being stirred for 7 hours under cooling with ice, the system was subjected to hydrolysis with addition of hydrochloric acid, followed by extraction with ether and drying of the resultant ether layer with anhydrous sodium sulfate. The dried product was distilled under normal pressure to obtain 9.46 g of 1,1,1-trifluoro-2-hexanone. Yield: 47%.

(2) Production of ethyl acetate-triphenylphosphonium bromide.

In a nitrogen atmosphere, 31.47 g (120 mM) of triphenylphosphine was added to 60 ml of benzene, and 23.38 g (140 mM) of ethyl bromoacetate was added under cooling with ice. After 1 hour of stirring at room temperature, the resultant precipitate salt was taken out by filtration and washed with benzene to obtain 48.90 g of ethyl acetate-triphenyl phosphonium bromide. Yield: 95%.

(3) Production of ethyl 3-trifluoromethyl-2-heptenoate.

In a nitrogen atmosphere, 2.83 g (123 mM) of metallic sodium was dissolved in 50 ml of ethanol, and excessive ethanol was distilled off. Thereto, 340 ml of methylene chloride and 52.71 g (123 mM) of ethyl acetate-triphenylphosphonium bromide prepared in advance were added, and the mixture was stirred for 1 hour. Then, 9.46 g (61.4 mM) of 1,1,1-trifluoro-2hexanone prepared above and dissolved in 5 ml of methylene chloride was added thereto, and the mixture was stirred for 46 hours. After addition of water, the product was extracted with methylene chloride, dried with anhydrous sodium sulfate and distilled under a reduced pressure to obtain 7.48 g of ethyl 3-tri-fluoromethyl-2-heptenoate. Yield: 54%.

(4) Production of 3-trifluoromethylheptanoic acid.

7.48 g of ethyl 3-trifluoromethyl-2-heptanoate was dissolved in 60 ml of metahnol, and 0.39 g of 5%-palladium/activated carbon was added thereto, followed by stirring for 4 hours at room temperature and normal pressure in a hydrogen atmosphere in a catalytic hydrogenation apparatus. After the reaction, the 5%-palladium/activated carbon was filtered out, and the remaining methanol solution was mixed with 60 ml of water and 7 g of potassium hydroxide, followed by 4 hours of heat refluxing, distilling-off of methanol under a reduced pressure, acidification with addition of 6N-hydrochloric acid, and extraction with diethyl ether. The resultant ether solution was dried on sodium sulfate, followed by distilling-off of the solvent and purification by distillation (b.p.: 118.5–119.7° C./20 mmHg), whereby 4.6 g of 3-trifluoromethylheptanoic acid was obtained. (yield: 63%).

(5) Optical resolution of 3-trifluoromethyl-1-heptanoic acid.

4.3 g of (±)-3-trifluoromethyl-1-heptanoic acid and 2.7 g of (−)-1-phenylethylamine were dissolved in a twice amount (weight ratio) of hexane under heating, followed by gradual cooling to precipitate a salt. The salt was taken out by filtration and subjected to two times of recrystallization from a twice amount of hexane. The salt was recovered in a yield of 1.6 g and showed a boiling point of 91–92° C., and $[\lambda]_D^{21}$ of −5.65 (c 1.95, methanol). The salt was dissolved in 1N-sodium hydroxide aqueous solution, and the amine was extracted with diethyl ether and removed. The remaining product was acidified with 2N-hydrochloric acid, and the carboxylic acid was extracted with diethyl ether. The ether solution was dried on magnesium sulfate and the solvent was distilled off to obtain 0.94 g (yield: 22%) of (−)-3-trifluoromethyl-1-heptanoic acid, which showed $[\alpha]_D^{24.4}$ −4.05 (c 1.80, chloroform).

By using (+)-1-phenylethylamine in place of the (−)-1-phenylethylamine in the above operation, (−)-3-trifluoromethyl-1-heptanoic acid can be obtained.

EXAMPLE 2

Production of (−)-3-trifluoromethyl-1-heptanol.

In a two-necked round-bottomed flask replaced with nitrogen, 0.09 g of lithium aluminum hydride and dry ether were placed and cooled with ice, and a solution of 0.5 g of (+)-3-trifluoromethyl-1-heptanoic acid in 3 ml of dry ether was added dropwise thereto. The mixture was stirred for 4 hours on an ice bath for reaction, and a saturated sodium sulfate aqueous solution was added thereto, followed by decantation to recover the ether layer. The ether solution was dried on sodium sulfate, followed by distilling-off of the solvent and distillation by means of a Kugelrohr distiller in the range of 96° C./33 mmHg–104° C./34 mmHg to obtain 290 mg (yield: 66%) of (−)-3-trifluoro-methyl-1-heptanol. $[\alpha]_D^{21}$ −2.3 (c 1, CHCl$_3$)

EXAMPLE 3

Optically active 3-trifluoromethylnonanoic acid was produced through the following reaction steps (1)–(5):

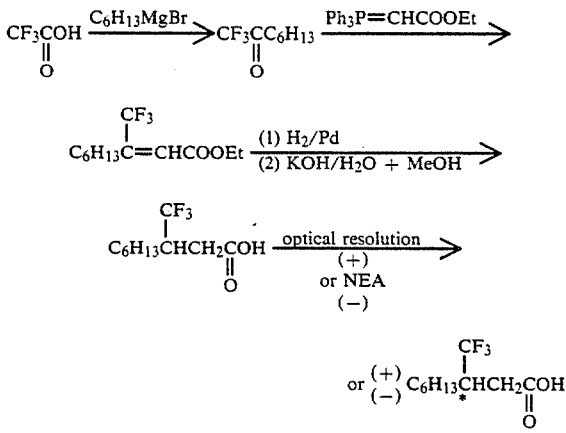

(1) Production of 1,1,1-trifluoro-2-octanone.

In a nitrogen atmosphere, 9.12 g (380 mM) of magnesium into 120 ml of ether, and 59.4 g (360 mM) of hexyl bromide dissolved in 30 ml of ether was added thereto, followed by 1.5 hours of heat refluxing. After cooling by standing and with ice, 13.68 g (120 mM) of trifluoroacetic acid dissolved in 30 ml of ether was added. After being stirred for 7 hours under cooling with ice, the system was subjected to hydrolysis with addition of hydrochloric acid, followed by extraction with ether and drying of the resultant ether layer with anhydrous sodium sulfate. The dried product was distilled under normal pressure to obtain 11.8 g of 1,1,1-trifluoro-2-octanone. Yield: 46%.

(2) Production of ethyl acetate-triphenylphosphonium bromide.

In a nitrogen atmosphere, 31.47 g (120 mM) of triphenylphosphine was added to 60 ml of benzene, and 23.38 g (140 mM) of ethyl bromoacetate was added under cooling with ice. After 1 hour of stirring at room temperature, the resultant precipitate salt was taken out by filtration and washed with benzene to obtain 48.90 g of ethyl acetate-triphenyl phosphonium bromide. Yield: 95%.

(3) Production of ethyl 3-trifluoromethyl-2-nonenoate

In a nitrogen atmosphere, 4.88 g (212 mM) of metallic sodium was dissolved in 80 ml of ethanol, and excessive ethanol was distilled off. Thereto, 544 ml of methylene chloride and 91.0 g (212 mM) of ethyl acetate-triphenylphosphonium bromide prepared in advance were added, and the mixture was stirred for 1 hour. Then, 19.35 g (106 mM) of 1,1,1-trifluoro-2-octanone prepared in advance and dissolved in 10 ml of dry benzene was added thereto, and the mixture was stirred for 48 hours. After addition of water, the product was extracted with methylene chloride, dired with anhydrous sodium sulfate and distilled under a reduced pressure to obtain 13.78 g of ethyl 3-tri-fluoromethyl-2-nonenoate. Yield: 54.6%.

(4) Production of 3-trifluoromethylnonenoic acid.

13.78 g of ethyl 3-trifluoromethyl-2-nonenoate was dissolved in 138 ml of methanol, and 1.38 g of 5%-palladium/activated carbon was added thereto, followed by stirring for 4 hours at room temperature and normal pressure in a hydrogen atmosphere in a catalytic hydrogenation apparatus. After the reaction, the 5%-palladium/activated carbon was filtered out, and the remaining methanol solution was mixed with 24 ml, of water and 20 g of potassium hydroxide, followed by 2 hours of heat refluxing, distilling-off of methanol under a reduced pressure, acidification with addition of 6N-hydrochloric acid, and extraction with methylene chloride. The resultant methylene chloride solution was dried on sodium sulfate, followed by distilling-off of the solvent and purification by distillation (b.p.: 118.5–119.7° C./20 mmHg), whereby 13.78 g of 3-trifluoromethylnonenoic acid was obtained. (Yield: 51.5%).

(5) Optical resolution of 3-trifluoromethyl-1nonanoic acid.

9.15 g (40.5 mM) of (±)-3-trifluoromethyl-1nonanoic acid and 6.24 g (36.5 mM) of (+)-1-naphthylethylamine were dissolved in 5 ml of hexane under heating, followed by gradual cooling to precipitate a salt. The salt was taken out by filtration and subjected to two times of recrystallization. The salt was recovered in an amount of 3.00 g (7.55 mM) and the yield was 38.0% of a half amount of the racemate.

The sparingly soluble salt showed the following properties:

$[\alpha]_{589}$ +3.40° (c 1.03, chloroform)

Melting point: 103–107° C.

From the salt, 1.32 g (5.84 mM) of 3-tri-fluoromethyl-1-nonanoic acid was isolated. Yield: 28.1%.

$[\alpha]_{589}$ −4.75° (c 4.02, chloroform).

By using (−)-1-naphthyl-1-ethylamine in place of the (+)-1-naphthyl-1-ethylamine in the above operation, (−)-3-trifluoromethyl-1-nonanoic acid can be obtained.

EXAMPLE 4

Production of (+)-3-trifluoromethyl-1-nonanol.

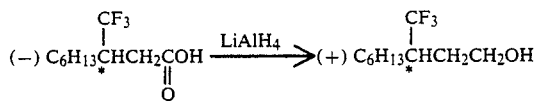

In a two-necked round-bottomed flask replaced with nitrogen, 67 mg of lithium aluminum hydride and dry ether were placed and cooled with ice, and a solution of 0.41 g of (+)-3-trifluoromethyl-1-nonanoic acid in 2 ml of dry ether was added dropwise thereto. The mixture was stirred for 4 hours on an ice bath for reaction, and a saturated sodium sulfate aqueous solution was added thereto, followed by decantation to recover the ether layer. The ether solution was dried on sodium sulfate, followed by distilling-off of the solvent and distillation by means of a Kugelrohr distiller at 110° C./28 mmHg to obtain 290 mg (yield: 66%) of (+)-3-trifluoromethyl-1-nonanol. $[\alpha]_D^{28}$ +1.82 (c 6.03, CHCl$_3$).

EXAMPLE 5

A glass substrate provided with an ITO (indium tin oxide) transparent electrode film was coated with a polyimide resin precursor (SP-510, mfd. by Toray K.K.), followed by heating at 300° C. for 60 minutes to form a polyimide film. Then, the film was orientation-treated by rubbing. Two glass substrates thus treated were fixed to each other so that their rubbing-treated axes crossed each other at right angles, thereby to form a blank cell with a cell gap of 8 μm. The cell was filled with a nematic liquid crystal composition (Lixon GR-63, a biphenyl liquid crystal mixture available from Chisso K.K.) to form a TN (twisted nematic)-type cell. When observed through a polarizing microscope, the TN-type cell showed a fringe pattern due to occurrence of reverse domain.

A liquid crystal composition was prepared by adding 1 wt. part of the optically active compound obtained by the above Example 2 to 99 wt. parts of the above Lixon GR-63 and used for preparation of a TN cell in the same manner as above. As a result of observation through a polarizing microscope, no reverse domain was observed but a uniform nematic phase was observed in the TN cell. From this fact, the optically active compound of the invention was found to be effective for prevention of reverse domain.

EXAMPLE 6

A TN cell prepared by using a liquid crystal composition prepared by mixing 1 wt. part of the optically active compound obtained in the above Example 1 with 99 wt. parts of p,p'-pentylazoxybenzene was observed to provide a nematic phase with remarkably reduced reverse domain as compared with a TN cell prepared without adding the optically active compound.

EXAMPLE 7

A liquid crystal mixture was prepared by adding 5 wt. parts of the optically active compound according to the above Example 2 to 95 wt. parts of a smectic liquid crystal MORA 8 having a structure as shown below. The liquid crystal mixture showed an SmC* phase, and showed a spontaneous polarization 1.8 times that of MORA 8 alone and a response time of 25 msec, about 60% of that of MORA 8 alone, under the voltage application condition of ±15 V.

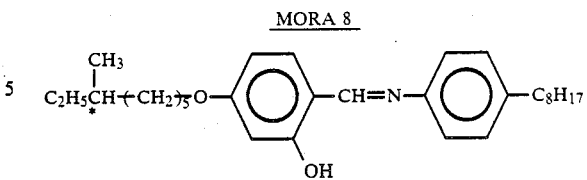

EXAMPLE 8

P-(3-trifluoromethylheptyloxy)phenol was prepared through the following steps (1) and (2).

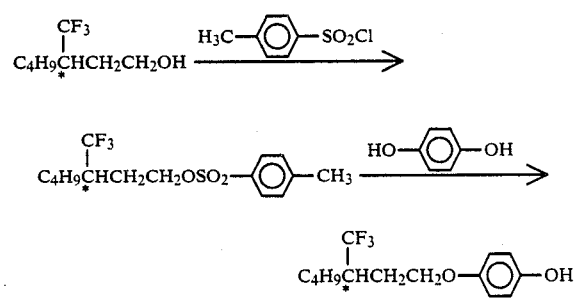

(Step 1) Production of 3-trifluoromethylheptyl-p-toluenesulfonate.

0.48 g of 3-trifluoromethyl-1-heptanol was dissolved in 0.79 g of pyridine, and the solution was cooled with ice, followed by addition of 0.5 g of p-toluenesulfonyl chloride, stirring for 2 hours under cooling with ice and stirring for 2 hours at room temperature. After the reaction, the product was acidified with 2N-hydrochloric acid and extracted with methylene chloride. The resultant methylene chloride solution was washed with water and dried with magnesium sulfate, and the solvent was distilled off, whereby 3-trifluoromethylheptyl p-toluenesulfonate was obtained in an amount of 0.82 g (yield: 92%) and showed: $[\alpha]_D^{23}$ +0.5, $[\alpha]_{435}^{23}$ +2.2 (c 2, methylene chloride).

(Step 2) Production of p-(3-trifluoromethylheptyloxy)phenol.

0.39 g of the above-obtained 3-trifluorometylheptyl p-toluenesulfonate and 0.25 g of hydroquinone were dissolved in 1 ml of butanol. To the solution was added a solution of 0.07 g of sodium hydroxide in 2 ml of butanol, followed by 5 hours of stirring at 130° C. for reaction. Then, water and 1N-hydrochloric acid were added to the reaction solution, followed by extraction with diethyl ether. The ether solution was dried with sodium sulfate, and the solvent was distilled off. The product was then purified by thin layer chromatography with methylene as the developer to obtain 0.17 g (yield:54%) of p-(3trifluoromethylheptyloxy)phenol which showed: $[\alpha]_D^{26}$ −2.8, $[\alpha]_{435}^{26}$ −4.9 (c 1, methylene chloride).

EXAMPLE 9

P-(3-trifluoromethylheptyloxy)benzoic acid was produced through the following steps

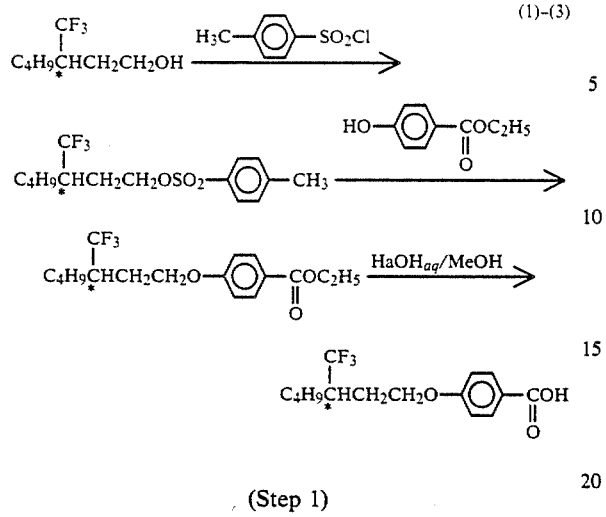

(1)-(3)

(Step 1)

3-trifluoromethylheptyl p-toluenesulfonate was prepared in the same manner as in Step (1) of Example 8.

(Step 2) Production of ethyl p-(3-trifluoromethyl-heptyloxy)benzoate.

0.54 g of 3-trifluoromethylheptyl p-toluene-sulfonate obtained in Step (1), 0.27 g of ethyl p-hydroxybenzoate and 1 ml of dimethylformamide (DMF) were placed in a round-bottomed flask, and 0.07 g of sodium 60%-hydride was added thereto together with DMF, followed by 6 hours of stirring at 130° C. After the reaction, DMF was distilled off under a reduced pressure, and water was added, followed by extraction with diethyl ether. The ether solution was dried with sodium sulfate, followed by distilling-off of the solvent to obtain 0.62 g of a crude product. The crude product was then purified by thin layer chromatography with benzene as the developer to obtain 0.22 g of ethyl p-(3-trifluoromethylheptyloxy)benzoate (yield: 42%).

(Step 3) Production of p-(3-trifluoromethylheptyloxy)benzoic acid.

0.082 g of sodium hydroxide was dissolved in 1 ml of water, followed by addition of 3 ml of methanol and 0.22 g of ethyl p-(3-trifluoromethylheptyloxy)benzoate and 3 hours of stirring at 50° C. After the reaction, water was added, methanol was removed by distillation under a reduced pressure, and 6N-hydrochloric acid was added to precipitate a crystal. The crystal was recovered by filtration, washed with water and dried to obtain 0.15 g (yield: 76%) of p-(3trifluoromethylheptyloxy)benzoic acid, which showed: $[\alpha]_D^{24}$ +4.2, $[\alpha]_{435}^{25}$ +8.6 (c 1.00, CHCl$_3$).

EXAMPLE 10

P-(3-trifluoromethylnonyloxy)benzoic acid was produced through the following steps.

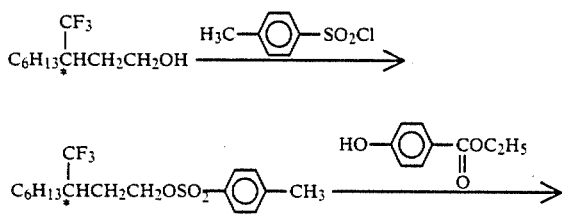

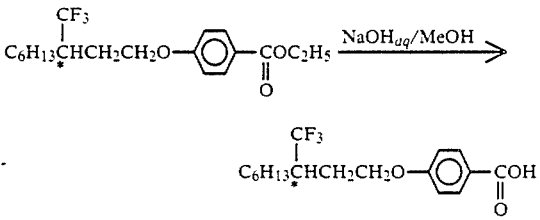

(Step 1) Production of 3-trifluoromethylnonyl p-toluenesulfonate.

3.08 mg of 3-trifluoromethyl-1-nonanol was dissolved in 453 mg of pyridine, and the solution was cooled with ice, followed by addition of 276 mg of p-toluenesulfonic chloride, stirring for 2 hours under cooling with ice and stirring overnight at room temperature. After the reaction, the product was acidified with 2N-hydrochloric acid and extracted with diethyl ether. The resultant diethyl ether solution was washed with water and dried with magnesium sulfate, and the solvent was distilled off. The crude product was purified by thin layer chromatography with benzene as the developer to obtain 345 mg (yield: 65%) of 3-trifluoromethylnonyl p-toluenesulfonate, which showed: $[\alpha]_D^{28}$ +1.63 (c 5.04, CHCl$_3$).

(Step 2) Production of ethyl p-(3-trifluoromethylnonyloxy)benzoate.

345 mg of 3-trifluoromethylnonyl p-toluenesulfonate obtained in Step (1), 166 mg of ethyl p-hydroxybenzoate and 1 ml of dimethylformamdie (DMF) were placed in a round-bottomed flask, and 80 mg of sodium hydride (60%) was added thereto together with DMF, followed by 6 hours of stirring at 130° C. After the reaction, DMF was distilled off under a reduced pressure, and water was added, followed by extraction with methylene chloride. The methylene chloride solution was dried with magnesium sulfate, followed by distilling-off of the solvent and purification by thin layer chromatography with benzene as the developer to obtain 205 mg of ethyl p-(3-trifluoromethylnonyloxy)benzoate (yield: 60.5%).

(Step 3) Production of p-(3-trifluoromethylnonyloxy)benzoic acid.

72 mg of sodium hydroxide was dissolved in 0.5 ml of water, followed by addition of 0.5 ml of methanol and 205 mg of ethyl p-(3-trifluoromethylnonyloxy)benzoate and 4 hours of stirring at 50° C. After the reaction, water was added, methanol was removed by distillation under a reduced pressure, and 2N-hydrochloric acid was added, followed by extration with diethyl ether. The ether solution was dried with sodium sulfate, and the solvent was distilled off to obtain 146 mg of optically active p-3-trifluoromethylnonyloxy)benzoic acid (yield: 77.2%).

EXAMPLE 11

A liquid crystal mixture was prepared by adding 5 wt. parts of the optically active compound according to the above Example 8 to 95 wt. parts of a smectic liquid crystal MORA 8 having a structure as shown below. The liquid crystal mixture showed an SmC* phase, and showed a spontaneous polarization 1.8 times that of MORA 8 alone and a response time of 25 msec, about 60% of that of MORA 8 alone, under the voltage application condition of ±15 V.

MORA 8

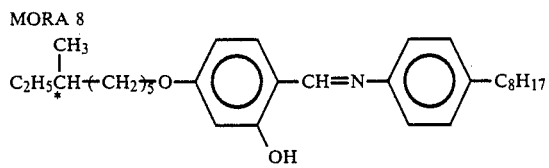

EXAMPLE 12

A glass substrate provided with an ITO transparent electrode film was coated with a polyimide resin precursor (SP-510, mfd. by Toray K.K.), followed by heating at 300° C. for 60 minutes to form a polyimide film. Then, the film was orientation-treated by rubbing. Two glass substrates thus treated were fixed to each other so that their rubbing treated axes crossed each other at right angles, thereby to form a blank cell with a cell gap of 8 μm. The cell was filled with a nematic liquid crystal composition (Lixon GR-63, a biphenyl liquid crystal mixture available from Chisso K.K.) to form a TN (twisted nematic)-type cell. When observed through a polarizing microscope, the TN-type cell showed a fringe pattern due to occurrence of reverse domain.

A liquid crystal composition was prepared by adding 1 wt. part of the optically active compound obtained by the above Example 8 to 99 wt. parts of the above Lixon GR-63 and used for preparation of a TN cell in the same manner as above. As a result of observation through a polarizing microscope, no reverse domain was observed but a uniform nematic phase was observed in the TN cell. From this fact, the optically active compound of the invention was found to be effective for prevention of reverse domain.

What is claimed is:

1. An optically active 3-trifluoromethyl alkanoic acid represented by the following formula (2):

wherein R denotes an alkyl group having 1-14 carbon atoms, and C* denotes an asymmetric carbon atom.

2. A liquid crystal composition comprising:
a liquid crystal material selected from the group consisting of nematic, chiral nematic, smectic and chiral smectic liquid crystals, and at least one species of optically active 3-trifluoromethyl alkanoic acid represented by

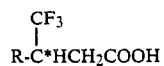

wherein R is $C_{1-14}$ alkyl and C* denotes an asymmetric carbon atom.

3. An alkanoic acid according to claim 1, wherein R is $C_{4-6}$ alkyl.

4. A composition according to claim 2, wherein R is $C_{4-6}$ alkyl.

* * * * *

UNITED STATES PATENT AND TRADEMARK OFFICE
CERTIFICATE OF CORRECTION

PATENT NO. : 4,917,817
DATED : April 17, 1990
INVENTOR(S) : HIROYUKI NOHIRA ET AL.              Page 1 of 3

It is certified that error appears in the above-identified patent and that said Letters Patent is hereby corrected as shown below:

ON TITLE PAGE:

Other Publications,
    "Tetraheoron" should read --Tetrahedron--.

AT [57] ABSTRACT

"denotes" should read --Y denotes--.

AT [73] ASSIGNEE

"Assignee: Canon Kabushiki Kaisha, Tokyo, Japan"
    should read --Assignees: Canon Kabushiki Kaisha
    and Yamakawa Chemical Industry Co., Ltd.,
    both of Tokyo, Japan--.

COLUMN 8

Example 2, "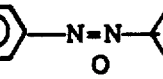   (2)"

should read

--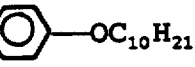   (2)"

UNITED STATES PATENT AND TRADEMARK OFFICE
CERTIFICATE OF CORRECTION

PATENT NO. : 4,917,817
DATED : April 17, 1990
INVENTOR(S) : HIROYUKI NOHIRA ET AL.   Page 2 of 3

It is certified that error appears in the above-identified patent and that said Letters Patent is hereby corrected as shown below:

COLUMN 9

Line 4, "SmA smectic A phase" should read --SmA: smectic A phase--.
Line 5, "SMB smectic B phase" should read --SMB: smetic B phase--.
Line 6, "SMC smectic C phase" should read --SMC: smetic C phase--.
Line 7, "N nematic phase" should read --N: nematic phase--.
Line 8, "Iso. isotropic phase" should read --Iso.: isotropic phase--.
Line 50, "into" should read --dissolved in--.

COLUMN 10

Line 47, "twice" should read --twice that--.
Line 50, "twice" should read --twice that--.
Line 52, "$[\lambda]_D^{21}$" should read --$[\alpha]_D^{21}$--.
Line 60, "(-)-3-trifluoromethyl-1-heptanoic acid," should read --(+)-3-trifluoromethyl-1-heptanoic acid,--.
Line 61, "$[\lambda]_D^{24.4}$-4.05(c 1.80, chloroform)." should read --$[\alpha]_D^{24.4}$+4.05(c 1.80, chloroform).

COLUMN 11

Line 47, "into" should read --dissolved in--.

COLUMN 12

Line 43, "-1nonanoic" should read ---1-nonanoic--.
Line 46, "-1nonanoic" should read ---1-nonanoic--.

UNITED STATES PATENT AND TRADEMARK OFFICE
CERTIFICATE OF CORRECTION

PATENT NO. : 4,917,817
DATED : April 17, 1990
INVENTOR(S) : HIROYUKI NOHIRA ET AL.

Page 3 of 3

It is certified that error appears in the above-identified patent and that said Letters Patent is hereby corrected as shown below:

COLUMN 14

Line 49, "3-trifluorometylheptyl" should read --3-trifluoromethylheptyl--.

COLUMN 15

Line 52, "p-(3trifluoromethylhep-" should read --p-(3-trifluoromethylhep---.
Line 58, "steps." should read --steps (1)-(3).--.

Signed and Sealed this

Thirty-first Day of March, 1992

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,917,817
DATED : April 17, 1990
INVENTOR(S) : HIROYUKI NOHIRA, ET AL.

It is certified that error appears in the above-identified patent and that said Letters Patent is hereby corrected as shown below:

On the Title page, item [56] REFERENCES CITED

Under U.S. PATENT DOCUMENTS, insert:
--4,444,784  4/84  Hoffman--.

Signed and Sealed this

Twenty-fifth Day of May, 1993

Attest:

MICHAEL K. KIRK

*Attesting Officer*   Acting Commissioner of Patents and Trademarks